US009462941B2

(12) United States Patent
Palanker

(10) Patent No.: US 9,462,941 B2
(45) Date of Patent: Oct. 11, 2016

(54) METAMORPHOPSIA TESTING AND RELATED METHODS

(71) Applicant: THE BOARD OF TRUSTEES OF THE LELAND STANFORD JUNIOR UNIVERSITY, Stanford, CA (US)

(72) Inventor: Daniel Palanker, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/419,140

(22) PCT Filed: Aug. 5, 2013

(86) PCT No.: PCT/US2013/053609
§ 371 (c)(1),
(2) Date: Feb. 2, 2015

(87) PCT Pub. No.: WO2014/022850
PCT Pub. Date: Feb. 6, 2014

(65) Prior Publication Data
US 2015/0201832 A1    Jul. 23, 2015

Related U.S. Application Data

(60) Provisional application No. 61/679,636, filed on Aug. 3, 2012.

(51) Int. Cl.
*A61B 3/02*    (2006.01)
*A61B 3/00*    (2006.01)
*A61B 3/032*   (2006.01)

(52) U.S. Cl.
CPC ............ *A61B 3/032* (2013.01); *A61B 3/0025* (2013.01); *A61B 3/0033* (2013.01); *A61B 3/0091* (2013.01)

(58) Field of Classification Search
USPC .................................................. 351/200–246
See application file for complete search history.

(56) References Cited

U.S. PATENT DOCUMENTS

| 4,408,846 A | 10/1983 | Balliet |
| H293 H | 6/1987 | Task et al. |

(Continued)

FOREIGN PATENT DOCUMENTS

| JP | 2007-165976 A | 6/2007 |
| KR | 10-2005-0018732 A | 2/2005 |

(Continued)

OTHER PUBLICATIONS

Allergan, Inc.; VisionCheck (iTunes App Store); released Feb. 23, 2011; retrieved Dec. 9, 2014 from the Internet (https://itunes.apple.com/us/app/visioncheck/id420911054?mt=8).

(Continued)

*Primary Examiner* — Mohammed Hasan
(74) *Attorney, Agent, or Firm* — Shay Glenn LLP

(57) ABSTRACT

A visual distortion test is disclosed using a sequence of binary interactions with a mobile device, in which segments of the grid having no distortions are eliminated, and the segments with distortions are divided into smaller segments for further analysis. The test can quantify the visual distortion using a decreased number of steps, compared to sequential analysis of all the segments of the grid. The binary interaction or input to the mobile device is also easier for patients than graphic interactions with a conventional Amsler Grid. Early detection of changes in the visual distortion can enable the healthcare provider to individualize treatment, helping to prevent vision loss while minimizing visits to the office, discomfort, and expense.

7 Claims, 5 Drawing Sheets

(56) References Cited

U.S. PATENT DOCUMENTS

| | | | |
|---|---|---|---|
| 4,798,456 A | 1/1989 | Enoch et al. | |
| 5,129,720 A | 7/1992 | Jovicevic | |
| 5,565,949 A | 10/1996 | Kasha | |
| 5,568,209 A | 10/1996 | Priester et al. | |
| 5,589,897 A * | 12/1996 | Sinclair | A61B 3/024 351/223 |
| 5,596,379 A | 1/1997 | Kawesch | |
| 5,880,814 A | 3/1999 | McKnight et al. | |
| 5,892,570 A | 4/1999 | Stevens | |
| 5,941,874 A * | 8/1999 | Hohla | A61F 9/008 128/898 |
| 6,033,076 A | 3/2000 | Braeuning et al. | |
| 6,142,631 A | 11/2000 | Murdoch et al. | |
| 6,425,665 B2 | 7/2002 | Hayashi et al. | |
| 6,585,376 B1 * | 7/2003 | Matsumoto | A61B 3/032 351/239 |
| 6,656,131 B2 | 12/2003 | Alster et al. | |
| 7,220,000 B2 | 5/2007 | Alster et al. | |
| 7,275,830 B2 | 10/2007 | Alster et al. | |
| 7,357,508 B2 | 4/2008 | Suzuki | |
| 7,367,671 B2 | 5/2008 | Sabel | |
| 7,427,137 B2 | 9/2008 | Koppany | |
| 7,470,026 B2 | 12/2008 | Kaido et al. | |
| 7,520,611 B2 | 4/2009 | Franz et al. | |
| 7,665,847 B2 | 2/2010 | Alster et al. | |
| 7,748,846 B2 | 7/2010 | Todd | |
| 7,891,813 B2 | 2/2011 | Ogilvie | |
| 7,942,529 B2 | 5/2011 | Tanassi et al. | |
| 8,029,138 B2 | 10/2011 | Todd | |
| 8,047,652 B1 | 11/2011 | Collazo | |
| 8,322,857 B2 | 12/2012 | Barbur et al. | |
| 8,523,360 B2 | 9/2013 | Husain | |
| 8,702,238 B2 | 4/2014 | Berry et al. | |
| 8,793,142 B2 | 7/2014 | Fishman et al. | |
| 8,851,678 B2 | 10/2014 | Pelah et al. | |
| 8,881,058 B2 | 11/2014 | Ollivierre et al. | |
| 8,888,288 B2 | 11/2014 | Iravani et al. | |
| 2005/0124375 A1 | 6/2005 | Nowosielski | |
| 2007/0146631 A1 | 6/2007 | Sinclair et al. | |
| 2008/0309879 A1 | 12/2008 | Hirji | |
| 2009/0060287 A1 | 3/2009 | Hyde et al. | |
| 2011/0082704 A1 | 4/2011 | Blum | |
| 2011/0170068 A1 | 7/2011 | Dan-Gur | |
| 2011/0267577 A1 | 11/2011 | Verma | |
| 2012/0050685 A1 | 3/2012 | Bartlett et al. | |
| 2012/0050686 A1 | 3/2012 | Bartlett et al. | |
| 2012/0218285 A1 | 8/2012 | Crane | |
| 2012/0287163 A1 | 11/2012 | Djavaherian | |
| 2013/0083185 A1 | 4/2013 | Coleman | |
| 2013/0128229 A1 | 5/2013 | Huang | |
| 2013/0155376 A1 | 6/2013 | Huang et al. | |
| 2013/0194317 A1 | 8/2013 | Guillon et al. | |
| 2013/0235346 A1 | 9/2013 | Huang et al. | |
| 2013/0250246 A1 | 9/2013 | Shapiro | |
| 2013/0278895 A1 | 10/2013 | Pham et al. | |
| 2013/0301007 A1 | 11/2013 | Wolffsohn et al. | |
| 2014/0114208 A1 | 4/2014 | Smith et al. | |
| 2014/0132932 A1 | 5/2014 | Jung | |
| 2014/0211167 A1 | 7/2014 | Lewis | |
| 2014/0268060 A1 | 9/2014 | Lee et al. | |
| 2014/0285768 A1 | 9/2014 | Barnard et al. | |
| 2014/0285769 A1 | 9/2014 | Palanker et al. | |

FOREIGN PATENT DOCUMENTS

| | | | |
|---|---|---|---|
| KR | 10-2005-0114861 A | 12/2005 | |
| KR | 10-2006-0066967 A | 6/2006 | |
| WO | WO2013/078406 A1 | 5/2013 | |
| WO | WO2013/155002 A1 | 10/2013 | |
| WO | WO2013/170091 A1 | 11/2013 | |

OTHER PUBLICATIONS

Dok LLC; Eye chart professional (iTunes App Store); released Nov. 10, 2010; retrieved Dec. 9, 2014 from the internet (https://itunes.apple.com/us/app/id401851376?mt=8).

Fuso Precision; Amsler (iTunes App Store); released Oct. 28, 2010; retrieved Dec. 9, 2014 from the internet (https://itunes.apple.com/us/app/amsler/id396044848?mt=8).

Nead; Eyes Test (iTunes App Store); released Jan. 17, 2011; retrieved Dec. 9, 2014 from the Internet (https://itunes.apple.com/us/app/eyestest/id414652461?mt=8).

Notal Vision; A modern alternative to the Amsler Grid (product information); © 2011; 2 pgs. (retrieved from the internet: http://www.notalvision.com/amsler_grid.html); This web address was available to applicant(s) at least as of Sep. 28, 2012.

Notal Vision; The ForseeHome age-related macular degeneration monitoring process (product information); © 2011; 2 pgs. (retrieved from the internet: http://www.notalvision.com/how_forsee_program_works.html); This web address was available to applicant(s) at least as of Sep. 28, 2012.

Notal Vision; The technology behind the ForseeHome AMD monitor (product information); © 2011; 2 pgs. (retrieved from the internet: http://www.notalvision.com/foresee-home-technology.html); This web address was available to applicant(s) at least as of Sep. 28, 2012.

Sabina Technology, LLP; Macula Tester (iTunes App Store); released Feb. 15, 2010; retrieved Dec. 9, 2014 from the internet (https://itunes.apple.com/us/app/maculatester/id334312308?mt=8).

* cited by examiner

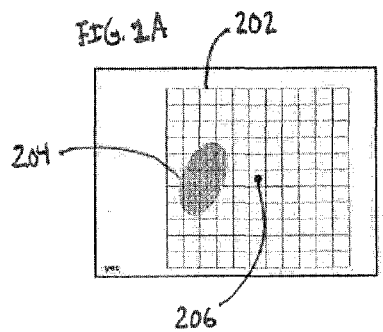
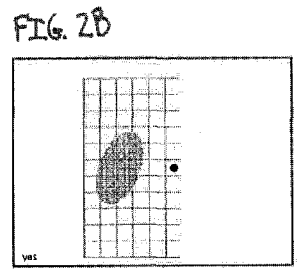
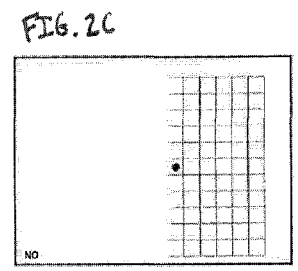
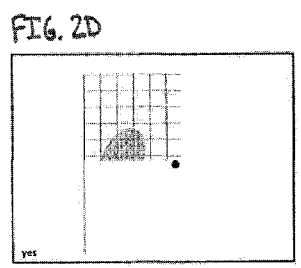
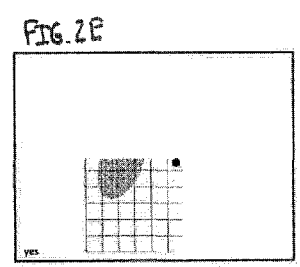
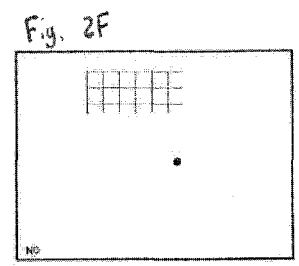
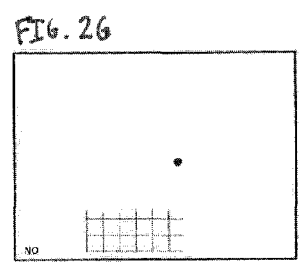
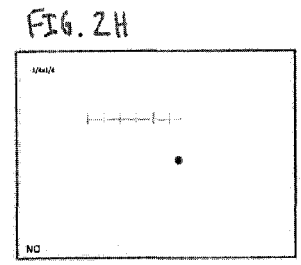
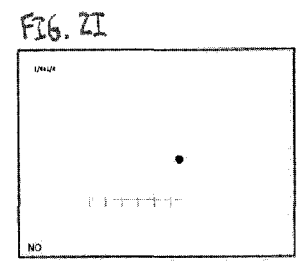
FIG. 2A  FIG. 2B  FIG. 2C
FIG. 2D  FIG. 2E  Fig. 2F
FIG. 2G  FIG. 2H  FIG. 2I

METAMORPHOPSIA TESTING AND RELATED METHODS

CROSS REFERENCE TO RELATED APPLICATIONS

This application claims the benefit of provisional application No. 61/679,636, filed on Aug. 3, 2012, the full disclosure of which is incorporated herein by reference.

The present disclosure is also related to provisional application No. 61/548,152 filed on Oct. 17, 2011, entitled "System and method for providing analysis of visual function using a mobile device with display," the disclosure of which is incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates generally to a system for analysis of visual function of a person using a mobile device with a display and communication capability, and method of use thereof. In various respects, the invention is directed to a system that allows patients to monitor their vision using a mobile device.

BACKGROUND

The use of portable devices to conduct visual acuity functions are known in the art, for example see U.S. Pat. No. 7,771,051, which is incorporated by reference in its entirety.

Additionally, the use of portable devices to conduct metamorphopsia tests using drawn inputs are known in the art, for example see U.S. Pat. No. 8,047,652, which is incorporated by reference in its entirety.

While portable devices exist, the current state of the testing methods used are time consuming. Moreover, the manner of interaction between user and device can be difficult for some users or adversely impact the accuracy of the testing. As a result there remains a need for improvement in the field of visual acuity testing.

Visual acuity testing, such as the Amsler grid, is commonly used for the detection of metamorphopsia—distortion of the image due to retinal detachment or edema. During metamorphopsia, a set of horizontal and vertical straight lines, appears wavy and parts of the grid may be absent or dim. Metamorphopsia is mainly associated with wet phase of age-related macular degeneration (i.e. choroidal neovascularization), pathological myopia, histoplasmosis syndrome, choroidal rupture and multifocal choroiditis.

During the conventional Amsler grid test patients are asked to look at the fixation point in the center of the grid, and mark the areas on the grid that appear distorted, absent, or dim. Even though the distortion is readily visible to patients, marking its location on the grid is often a very challenging task. The problem is that in some cases as soon as a person begins to draw his sight instinctively moves from the fixation point to the pen or a finger on a touch screen. This shifts the distorted area away, and the patient does not see the area he is marking as distorted anymore. Fixating away from the drawing tool (so called off-center fixation) requires significant cognitive effort which is often beyond the capabilities of the average patient affected by age-related macular degeneration. Typically, patients can easily tell whether they see distortions on the grid, but it can be hard to quantify the extent of these distortions by marking the grid. In some cases patients can have dexterity issues that make marking the grid accurately difficult or impractical.

Patients can be discouraged from taking tests on their own if the tests are difficult, time consuming, or have too many steps. As a result, it is desirable to design a test that is easy for the patient to take on their own time and that requires relatively few steps to achieve a useful result.

SUMMARY OF THE DISCLOSURE

Methods of testing visual distortions are provided herein. In some embodiments the methods can include (a) displaying a fixation point and a series of straight lines on a test area on a hand held computer device; (b) receiving a positive or negative input from a user indicating the presence or absence of distortion on the displayed series of straight lines on the test grid area; (c) removing any portions of the series of straight lines from the test area for which a negative input was received; (d) dividing the remaining positive test area into a plurality of segments; (e) sequentially displaying a fixation point and each of the plurality of segments on the hand held computer device. The steps (a)-(d) can be repeated until the segments of a predetermined minimum size are analyzed. The series of straight lines can include an Amsler grid. The method of testing distortions can be designed to test for metamorphopsia. The hand held computer device can include a mobile phone.

Examples of inputs include an auditory input or touching a discrete portion of the screen of the hand held computer device. In some embodiments the positive or negative input for presence or absence of distortion does not include touching a distorted area on the display.

The methods can also include repeating steps (a)-(d) until the visual distortion test area has been quantified with a desired level of precision to generate a visual distortion test result for the user. The methods can also include transmitting the visual distortion test results to a remote server. The methods can further include analyzing the visual distortion test results to determine a prediction of when further medical treatment is needed for the user. The methods can also include customizing the series of straight lines first presented to the user based on the user's previous visual distortion test results. In some embodiments the methods include preparing a resulting map of distortions from the visual distortion test results with segments of the predetermined minimum size.

In some embodiments dividing the remaining positive test area can include dividing the remaining positive test area by a factor of 2 or greater.

In some embodiments the series of straight lines can include moving horizontal and/or vertical lines.

In some embodiments methods of visual distortion testing are provided. The methods can include displaying a test grid area on a hand held computer device; receiving a positive or negative input from a user indicating the presence or absence of distortion on the test grid area; removing any portions of the test grid area from the test area for which a negative input was received; calculating a first remaining positive test area; dividing the first remaining positive test area into a first plurality of segments; sequentially displaying each of the first plurality of segments on the hand held computer device; receiving a negative or positive input from the user indicating the presence or absence of distortion for each of the first plurality of segments; removing any of the first plurality of segments from the first remaining positive test area for which a negative input was received; calculating a second remaining positive test area; dividing the second remaining positive test area into a second plurality of segments; sequentially displaying each of the second plurality of segments on the hand held computer device; receiving a negative or positive input from the user indicating the presence or absence of distortion for each of the second plurality of segments; and removing any of the second plurality of segments from the second remaining positive test area for which a negative input was received.

The methods can also include repeating the calculating, dividing, sequentially displaying, receiving, and removing steps until the visual distortion of the test grid has been quantified with a desired level of precision to generate a visual distortion test result for the user. The methods can further include transmitting the visual distortion test results from the hand held computing device to a remote network. The methods can also include analyzing the visual distortion test results and comparing the visual distortion test results to previous visual distortion test results. The methods can also include generating a notification message if the visual distortion test results indicate that the user may need a medical treatment.

In some embodiments dividing the remaining positive test area can include dividing the remaining positive test area by a factor of 2 or greater.

In some embodiments the visual distortion test can be customized based on the user's previous test results.

In some embodiments methods of testing visual distortions are provided. The methods can include (a) displaying a fixation point and an Amsler Grid on a hand held computer device; (b) receiving a positive or negative input from a user indicating the presence or absence of distortion on the displayed test grid area; (c) removing any portions of the grid from the test area for which a negative input was received; (d) dividing the remaining positive test area into a plurality of segments; (e) sequentially displaying a fixation point and each of the plurality of segments on the hand held computer device. The methods can also include repeating steps (a)-(d) until the segments of a predetermined minimum size are analyzed.

BRIEF DESCRIPTION OF THE DRAWINGS

A better understanding of the features and advantages of the present invention will be obtained by reference to the following detailed description that sets forth illustrative embodiments, in which the principles of the invention are utilized, and the accompanying drawings of which.

DETAILED DESCRIPTION

The present application discloses improved methods for administering metamorphopsia tests.

Distortions can be mapped quantitatively using an interactive computer-guided test instead of a printed grid. In this approach various parts, sections, portions, or segments of the grid appear on the screen, and the patient is only asked whether there is a distortion in the displayed segment of the grid or no distortion visible in the displayed segment. Since the patient is not asked to mark the actual position of the distortions on the screen, it is quite easy to keep his/her sight directed onto the fixation point, and just respond in a binary fashion, e.g. yes or no, whether the presented segment of the screen is distorted or not.

For mapping the whole field in this test, various segments of the grid can generally be presented in a sequence. To minimize the number of steps in this mapping procedure the size of the grid segments presented on the screen can decrease as the test progresses. Thereby large parts of the visual field that have no distortions can be quickly eliminated from further mapping.

The improved testing follows this general procedure. First, the whole grid is presented. A fixation spot (different from the rest of the grid in color or flashing or shape) is shown in the center of the grid. Next, if the patient looking at the fixation target sees no distortion, he responds by touching an area on the screen, such as a NO button (or any other label indicating the lack of distortion), or by a voice command and the test is completed. The area of the screen used to register a negative response can be a colored button or a button labeled with words indicating a negative response. If he does see a distortion he makes an affirmative response, such as by touching an area of the screen, which could be the fixation spot, a YES button, or a separate button (or section) on the screen, or by voice command. After the initial indication of distortion, any negative response to a displayed segment removes that segment from further testing. Thereafter, with every positive response the presented segment having distortion will be subsequently divided into smaller portions or segments, e.g. two halves and both of them will be presented sequentially. The divisions can be applied along the horizontal or vertical axis (or at any other direction). This way the non-distorted areas can be efficiently eliminated from the test mapping area. The distorted areas can be further tested until the distortion area is quantified with a desired level of precision or the distorted area is localized to the minimum size of the grid presented, for example, to a single square.

Figure 1:
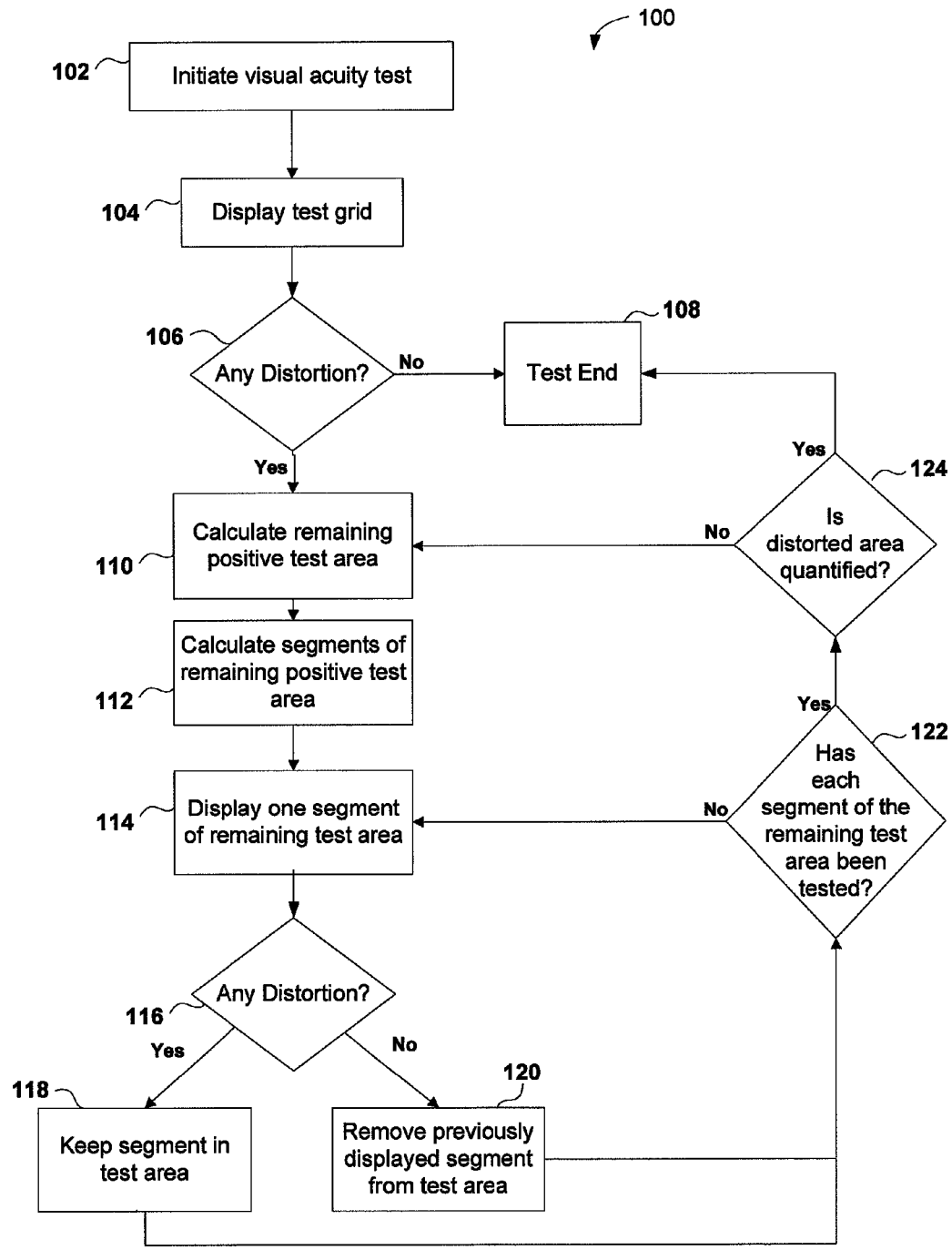
FIG. 1 is a flow chart of a method for performing a visual acuity test.

FIG. 1 is a flow chart of a method 100 for performing a visual acuity test in accordance with an embodiment. A first block 102 includes initiating a visual acuity test. The screen then displays a test grid 104, for example a test grid with a dot for a fixation point. The user is then queried whether any distortion is visible on the test grid in block 106. The user can answer by touching the screen or with an audible answer. If no distortion is visible then the test ends in block 108. If distortion is visible in the grid then the testing continues to gather additional data about the distortion size and shape.

In block 110, the remaining positive test area is calculated. After the first step, the remaining positive test area is the entire area or 100%. Next, the test area can be broken up into multiple segments for further analysis. Segments of the remaining test area are calculated in block 112. In some embodiments the test area is divided into halves. In some embodiments, a factor other than one-half can be used to reduce the test area size, for example by factors of 1.5, 2.5, 3, 4, etc.

Next, the program then displays one of the segments of the remaining test area (block 114) and queries the user whether there is any visible distortion (block 116). It is to be appreciated that the testing proceeds in binary fashion by answering a question, such as "Is there any distortion in the displayed segment?" If the user responds that there is visible distortion on the segment then the segment test area is added to the positive test area (block 118). If the user responds that there is no visible distortion then the segment test area is removed from the areas tested in the future tests (block 120). Next, in block 122 the program determines if each segment of the remaining test area has been tested. If the answer is no then an additional segment of the remaining test area is displayed (block 114). If all of the segments for the test area have been displayed then the results are analyzed to determine if the distorted area is sufficiently quantified (block 124). If the distorted area is sufficiently quantified then the test is ended (block 108).

In another aspect greater precision or fidelity of the area of distortion may be desired under the circumstances. If the distorted area is not sufficiently quantified then the remaining positive test area is again calculated or determined (block 110). The remaining test area is again split into segments (block 112) and displayed to the user (block 114) with the steps repeated until the distorted area is sufficiently quantified. In some embodiments, if further resolution of the distorted space is desired then additional testing can be performed to further determine the shape of the distortion, as discussed in greater detail below with respect to FIG. 3A-3K.

Figure 2J:
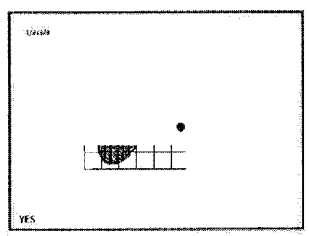
FIG. 2A-2P illustrate a schematic example of screen shots of performing a sample visual acuity test.
Figure 2K:
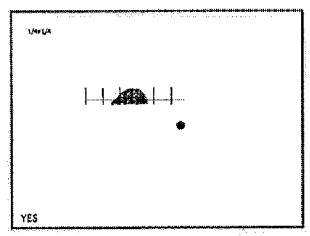
Figure 2L:
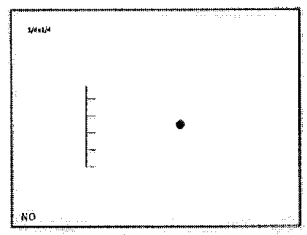
Figure 2M:
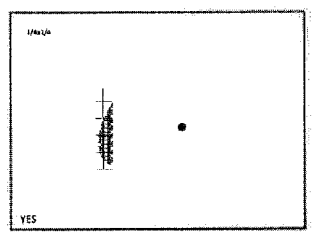
Figure 2N:
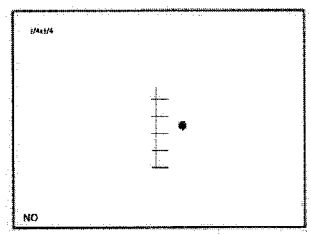
Figure 2O:
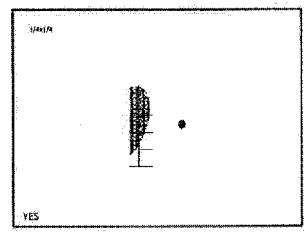
Figure 2P:
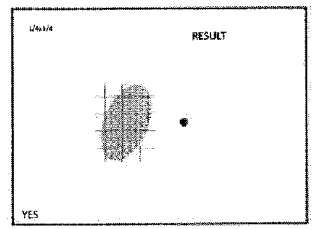
Figure 3A:
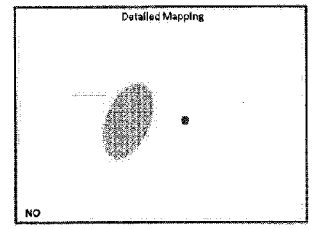
FIG. 3A-3K illustrate a schematic example of screen shots of performing a sample visual acuity test.
Figure 3B:
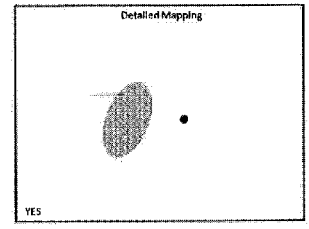
Figure 3C:
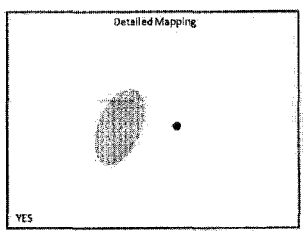
Figure 3D:
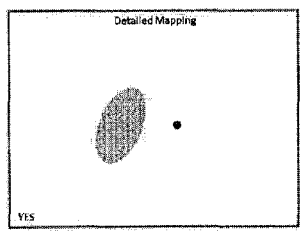
Figure 3E:
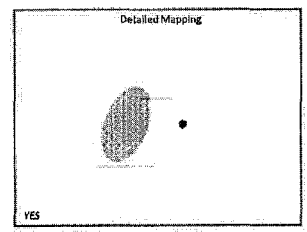
Figure 3F:
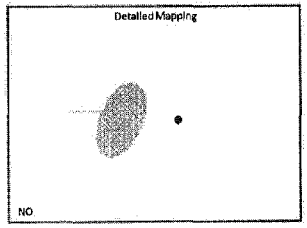
Figure 3G:
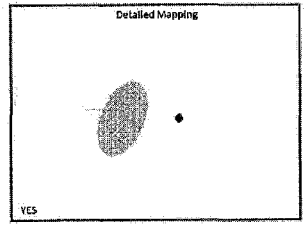
Figure 3H:
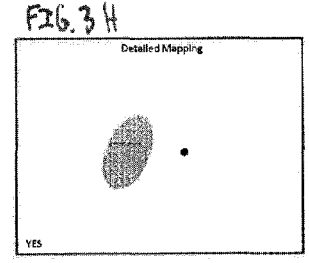
Figure 3I:
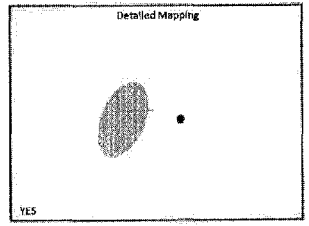
Figure 3J:
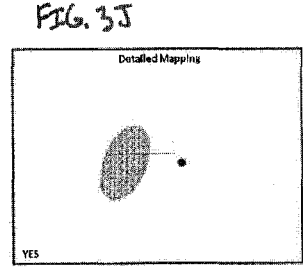
Figure 3K:
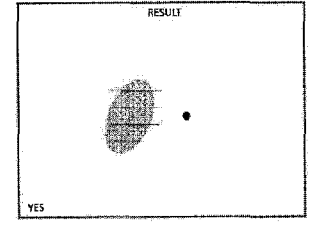

FIG. 2A-2P illustrate a schematic example of screen shots of performing a sample visual acuity test. FIG. 2A illustrates a complete test grid 202 showing a sample distorted area 204 and with a fixation point 206. For convenience the distorted area is represented as a shaded area 204. Distortion is present on the test grid in FIG. 2A so the user would respond with YES to indicate that distortion is present. The positive test area is calculated. At this point in this example, the remaining positive test area is the entire area. The positive test area is then divided into multiple segments. In this example, the positive test area is divided into two segments. The first of the two segments is displayed to the user in FIG. 2B. The user would respond in the affirmative that distortion is present in FIG. 2B. The segment shown in FIG. 2B would be kept in the test area. The grid (i.e., the other of the segments) in FIG. 2C would then be presented to the user. The user would answer in the negative because no distortion is present. The test area in FIG. 2C would be removed from the test area. Next the remaining test area would be calculated and split into two segments. The two segments of the remaining area, illustrated in FIGS. 2D and 2E are presented to the user. The user would answer in the affirmative that distortion is present on both FIGS. 2D and 2E. The remaining test area then includes the segments shown in FIGS. 2D and 2E. Each of the segments is divided into two, leaving four segments to be tested.

The program can determine an efficient way to present the four segments. For example, the program can assume that the distortions are continuous and potentially overlap the intersection of the test grid segments illustrated in FIGS. 2D and 2E. As a result the segments presented in FIGS. 2F and 2G are the segments that do not include the area where the segments in FIGS. 2D and 2E are likely to intersect. Here, the user would respond in the negative to the segments displayed in FIGS. 2F and 2G. The program can then assume that the distortion is present in both of the two segments that were not displayed in FIGS. 2F and 2G based on the positive responses to the segments in FIGS. 2D and 2E. The positive test area is now the area of FIG. 2D less area of FIG. 2F and area of FIG. 2e less area of FIG. 2G. The newly calculated test area can again be divided and further segments can be presented. FIGS. 2H and 2I present segments with the outer horizontal portions of the remaining test area. Negative responses remove those segments from the remaining test area. Next, the segments in FIGS. 2J and 2K are presented to the user, with the user responding that distortion is present. The logic can assume that the distorted area is continuous between the segments shown in FIGS. 2J and 2K and save steps by not presenting the space or segment between FIGS. 2J and 2K. FIGS. 2L-2O show the remaining test area split into vertical segments and presented to the user. The user responds in the negative to the segments in FIGS. 2L and 2N and in the positive to the segments shown in FIGS. 2M and 2O. The positive test area can then be represented by the grid shown in FIG. 2P. If the positive test area is sufficiently quantified then the test ends. If further resolution of the distorted space is desired then additional testing can be performed to further determine the shape of the distortion, as discussed in greater detail below with respect to FIG. 3A-3K.

The data on the distorted areas may be quantified using a number of different factors, such as, for example in the dimensions of an area of distribution, coordinates of all or a portion of the boundaries of a distortion area, the relative size, position or movement of a distortion area compared to prior patient data and the location relative to the fixation center, among others. The quantifying may be performed by a program operating onboard the device, by a mobile application or remotely by a server run application. Information related to test responses or the distorted area can be stored as coordinates corresponding to the grid sections covering the distorted area, as a picture, or as a percentage of the total test area. The data representing the distorted area can be stored on a mobile device and/or uploaded to a remote server or website.

The testing methods disclosed herein can be used to obtain a sufficiently precise representation of the distorted area for the purpose of evaluation of a patient condition. Generally, the size of the distortion and any information on whether the size of the distortion has changed with time is more useful to the physician than the precise size of the distortion. Typically, the size of the distortion area and/or location of the distortion correlates with the level of disease present or progression of disease or state of treatment in the user or patient. The change in the distortion area for the patient can be tracked over time to see how the patient's vision is changing and to determine whether treatment is effective or if additional treatment may be needed. The rate of change can also be used to predict when further patient treatment is needed.

The user can input the yes/no response to the test by touching the screen, by voice, by touching the screen with an object such as a stylus, or by other means. The fixation point 206 can be the area of the screen to touch to register a positive response so that the user does not have to move their eyes from the fixation point. In one aspect, a separate area of the screen can be touched to register a negative response.

As the test progresses the fixation point can shift from one position on the screen to another to allow displaying larger areas of the grid. For example, if a fixation point is shifted to the right edge of the screen, then the area displayed to the left of the fixation point is two times larger than the area available if the fixation point is presented in the center of the screen. By sequential positioning the fixation point into 4 corners of the screen a visual field 4 times larger (2×2) than the screen size can be mapped.

The program/logic implementing an embodiment of the metamorphopsia test described herein can be used to minimize the number of steps required to achieve a useful result. The program can make various assumptions to more efficiently determine the size and shape of the distorted area. For example, the program can assume that an area of distortion is continuous. The program can skip segments in some cases if the previous data indicates that a distortion is present. For example, after the negative responses to the segments in FIGS. 2F and 2G, the program assumed that there was a distortion in the area between the segments in FIGS. 2F and 2G based on the positive responses to the segments shown in FIGS. 2D and 2E. In this example, the program can move to block 124 or 110 from block 122 instead of continuing with block 114 to reduce steps.

The program can switch between horizontal and vertical segmentation. See for example the change in segments displayed between FIGS. 2K and 2L. The program can determine when it is efficient to switch between horizontal and vertical segmentation. Segmentation can also be performed using non-orthogonal axes. For example, using lines crossing at 60° rather than a rectangular grid.

The program can change the division factor when calculating the segments of the remaining test area in block 112. FIG. 2A-2P generally illustrates a division factor of 2. The division factor can vary. In some embodiments the division factor can be about 1.5, 2, 2.5, 3, 4, 5, 6, 7, 8, 9, 10, or any other integer. In some embodiments the division factor can be expressed as a percentage, such as 30%, 40%, 60%, or 70% depending on a number of factors. The division factor can be modified by the program during the test, such as by starting out with a lower division factor, e.g. 2, and later increasing the division factor, e.g. to about 3. Or vice-versa, the division factor can be higher during the beginning of the test and later be decreased. In some embodiments, the division factor can be optimized to achieve a sufficiently quantitative characterization of the distorted area in a relatively low number of steps. In some embodiments, the division factor can be optimized to achieve a more precise quantitative characterization of the distorted area.

Figure 4:
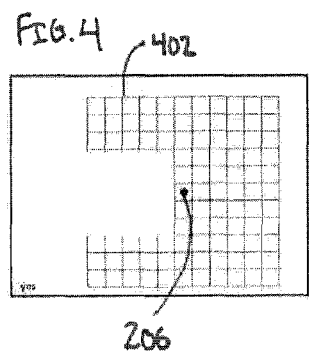
FIG. 4 illustrates a schematic example of screen shot of performing a sample visual acuity test.

In some embodiments the program can take into account patient data when determining what areas of the grid to display to patients. For example, the program can tailor the test based on the patient disease type, previous patient testing data (e.g. location or size of previous distortion and/or rate of change of the distortion size), and any other patient information. The test can be tailored to efficiently determine if the previous distortion has changed size, shape, or location. The initial presentation segment to the patient could be a larger area that excludes the area around the distorted area from the last test, for example the initially displayed segment could be ¾ of the total test area. Consider an example where prior testing indicated a distortion area is at it appears in FIG. 2A. The first test area presented 402 may be as shown in FIG. 4. A response of "no distortion" to this screen approximates the current test result based on the prior result. Thereafter, segments may be applied as discussed above to determine whether the distortion area has changed size, shape or location within the generally known distortion area. As this example demonstrates, a test pattern modeled on prior results can remove ¾ of the test area with a negative response. Additional steps to further determine the size and shape of the distortion may follow.

In some embodiments the program can modify the distance between the horizontal lines and vertical lines to make a finer grid structure in the displayed test area. The finer grid structure can be used to increase the precision of the distorted area in comparison to using larger grid structures. The resolution of the test would correspond to the size of the squares on the grid. Adding additional lines to form a finer grid structure can increase the precision of the distorted area.

Figure 5A:
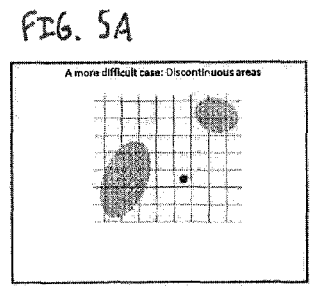
FIG. 5A-5B illustrate a schematic example of sample test results for a visual acuity test.
Figure 5B:
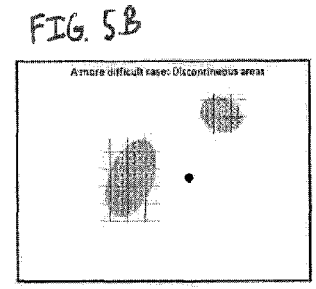

The program can be used to identify multiple distortion spots, such as the distortion spots illustrated in FIGS. 5A and 5B. If the program identifies that multiple areas may be present then the program can be used to analyze one of the distortions followed by analyzing the other distortion in sequence.

In some case it can be desirable to achieve a more precise representation of the distortion. It is harder to see distortions in small segments of straight lines so the division may stop at segments larger than a single square and an additional mapping algorithm can be applied. In this approach horizontal or vertical lines are presented in the area overlapping with the area marked as distorted. The length of these lines correspond to several periods of the grid. The line(s) shift by one period with each positive response until the distortion disappears (i.e. a negative response is obtained). This approach allows mapping the grid with the precision of one period, while the presented segments can be much longer.

If additional precision is desired for the quantitative result achieved in FIG. 2P then additional line mapping can be performed using horizontal and/or vertical lines. An example of additional mapping is shown in the flow chart illustrated in FIG. 3A-3K. A horizontal line can move horizontally across the test area determined as distorted by previous testing. FIG. 3A-3E illustrate a horizontal line moving across the test area between discrete points. The patient responds with an affirmative response if any distortion is present on the displayed line. The patient would respond in the negative for FIG. 3A and in the affirmative for FIG. 3B-3E. After testing a particular horizontal latitude the distortion can be tested for a different horizontal latitude as shown in FIG. 3F-3J. The patient would respond in the negative for FIG. 3F and in the affirmative for FIG. 3G-3J. Additional horizontal mapping could be used to further determine the shape of the distortion. The program can continue until a sufficiently precise data is achieved.

In some embodiments vertical line mapping is used. In some embodiments horizontal line mapping is used. In some embodiments a combination of horizontal and vertical line mapping can be used. The program can be configured to use horizontal and vertical mapping to achieve a desired resolution on the distortion in a minimum number of steps. The program can also be configured to switch between horizontal and vertical modes. Lines at orientations other than horizontal or vertical can also be used. For example, a non-orthogonal set of lines (e.g. crossing at 60 degrees) can also be used.

The testing methods disclosed herein can result in improvements over current metamorphopsia tests in several aspects. First, the testing methods disclosed herein can deliver results in a form that is similar to the traditional format familiar to all ophthalmologists, and thereby is easily understood and interpreted by the doctors. Second, the algorithm is based on reduction of the segments size as the test progresses, thereby eliminating the large non-distorted sections before more refined mapping of the distorted areas is performed. This approach allows for minimizing the number of steps and time that would be required, compared to the more traditional approach of hyperacuity testing that use small segments throughout the whole visual field to map distortions. Third, the patient input can be registered by touching the fixation point or speaking the result thereby reducing foveal scanning and eye movement away from the fixation point. Fourth, the testing methods disclosed herein can leverage the familiar grid-like structure while still creating sufficient quantitative precision to detect changes in visual distortion over time using a relatively small number of steps. The testing methods can be performed on a portable device thereby allowing the patients to do the tests on their own. Periodic testing (i.e., daily or weekly or on a set schedule or frequency) can be used to track changes in the user's visual acuity over time.

The testing methods described herein can make it easier for patients to do testing on their own. The binary response, e.g. yes or no, makes the tests easier to take versus tests that require touching distorted areas or drawing over the distorted areas or choosing between three or more possible responses. The tests are also quicker than previous testing methods because the distortion can be determined without detailed mapping of the entire test area. The removal of the non-distorted areas (regions of non-interest) hastens the result and permits use of coarser segments initially with increasing segment fidelity as the region of interest becomes better defined. The reduced number of steps and quicker tests can also make the tests easier on users. Making the tests easier for the user or patient can encourage the users to periodically take the tests. The user data for a particular test over a period of time can be useful for calculating and analyzing trends in the change in the user's metamorphopsia. The trending data can be used to determine if and when additional treatment may be useful for the patient. The ability to predict when additional treatment may be useful can save the user money and time by avoiding wasted doctor visits. The trending data can also be useful to determine if the selected course of treatment is achieving the desired results or whether a different treatment schedule may be useful.

The foregoing detailed description of the technology herein has been presented for purposes of illustration and description. It is not intended to be exhaustive or to limit the technology to the precise form disclosed. Many modifications and variations are possible in light of the above teaching. The described embodiments were chosen in order to best explain the principles of the technology and its practical application to thereby enable others skilled in the art to best utilize the technology in various embodiments and with various modifications as are suited to the particular use contemplated. The present invention descriptions are intended to cover such alternatives, modifications, and equivalents as may be included within the spirit and scope of the invention as defined by the appended claims and otherwise appreciated by one of ordinary skill in the art.

What is claimed is:

1. A method of visual distortion testing, the method comprising:

displaying a test grid area on a hand held computer device;

receiving a positive or negative input from a user indicating the presence or absence of distortion on the test grid area;

removing any portions of the test grid area from a test area for which a negative input was received;

calculating a first remaining positive test area;

dividing the first remaining positive test area into a first plurality of segments;

sequentially displaying each of the first plurality of segments on the hand held computer device;

receiving a negative or positive input from the user indicating the presence or absence of distortion for each of the first plurality of segments;

removing any of the first plurality of segments from the first remaining positive test area for which a negative input was received;

calculating a second remaining positive test area;

dividing the second remaining positive test area into a second plurality of segments;

sequentially displaying each of the second plurality of segments on the hand held computer device;

receiving a negative or positive input from the user indicating the presence or absence of distortion for each of the second plurality of segments; and removing any of the second plurality of segments from the second remaining positive test area for which a negative input was received.

2. The method of claim 1, further comprising repeating the calculating, dividing, sequentially displaying, receiving, and removing steps until the visual distortion of the test grid has been quantified with a desired level of precision to generate a visual distortion test result for the user.

3. The method of claim 2, further comprising transmitting the visual distortion test results from the hand held computing device to a remote network.

4. The method of claim 3, further comprising analyzing the visual distortion test results and comparing the visual distortion test results to previous visual distortion test results.

5. The method of claim 4, further comprising generating a notification message if the visual distortion test results indicate that the user may need a medical treatment.

6. The method of claim 1, wherein dividing the remaining positive test area includes dividing the remaining positive test area by a factor of 2 or greater.

7. The method of claim 1, wherein the visual distortion test is customized based on the user's previous test results.

* * * * *